United States Patent
Coury et al.

(10) Patent No.: US 6,261,544 B1
(45) Date of Patent: Jul. 17, 2001

(54) POLY(HYDROXY ACID)/POLYMER CONJUGATES FOR SKIN APPLICATIONS

(75) Inventors: Arthur J. Coury, Boston; Luis Z. Avila, Arlington; Chandrashekhar P. Pathak, Waltham; Shikha P. Barman, Lowell, all of MA (US)

(73) Assignee: Focal, Inc., Lexington, MA (US)

( * ) Notice: Subject to any disclaimer, the term of this patent is extended or adjusted under 35 U.S.C. 154(b) by 0 days.

(21) Appl. No.: 09/249,841

(22) Filed: Feb. 15, 1999

Related U.S. Application Data

(62) Division of application No. 08/739,644, filed on Oct. 30, 1996, now Pat. No. 5,879,688, which is a division of application No. 08/401,931, filed on Mar. 9, 1995, now Pat. No. 5,618,850.

(51) Int. Cl.[7] .......................... A61K 31/765; A61K 7/48
(52) U.S. Cl. .......................... 424/78.02; 424/43; 424/47; 424/59; 424/65; 424/69; 424/78.03; 424/78.05; 424/78.06; 424/78.07; 424/78.17; 424/78.18; 424/78.19; 424/405; 424/407; 424/420; 424/486; 424/401; 525/411; 525/413; 525/450; 514/772.5; 514/772.6; 514/772.7; 514/830; 514/887; 514/919; 514/944; 514/945; 514/947; 514/969; 514/772.1; 514/772.3; 514/772.4
(58) Field of Search .......................... 424/401, 400, 424/78.02, 78.03, 78.05–78.07, 78.17–78.19, 405–407, 420, 486–488, 43, 46, 47, 59, 65, 69; 514/772.1–772.7, 830, 887, 919, 944, 945, 947, 969; 525/411–413, 450

(56) References Cited

U.S. PATENT DOCUMENTS

| | | |
|---|---|---|
| 2,726,982 | 12/1955 | Ochs et al. . |
| 2,917,410 | 12/1959 | Vitalis . |
| 3,689,531 | 9/1972 | Critchfield et al. . |
| 3,739,773 | 6/1973 | Schmitt et al. . |
| 3,755,558 | 8/1973 | Scribner et al. . |
| 3,784,585 | 1/1974 | Schmitt et al. . |
| 3,988,470 | 10/1976 | Van Scott et al. . |
| 4,105,782 | 8/1978 | Yu et al. . |
| 4,234,599 | 11/1980 | Van Scott et al. . |
| 4,273,873 * | 6/1981 | Sugitachi et al. ..................... 435/180 |
| 4,294,852 | 10/1981 | Wildnauer et al. . |
| 4,363,815 | 12/1982 | Yu et al. . |
| 4,380,549 | 4/1983 | Van Scott et al. . |
| 4,526,938 | 7/1985 | Churchill et al. . |
| 4,563,489 | 1/1986 | Urist . |
| 4,668,430 | 5/1987 | Schmolka . |
| 4,673,571 | 6/1987 | Mahieu et al. . |
| 4,826,945 | 5/1989 | Cohn et al. . |
| 4,857,602 | 8/1989 | Casey et al. . |
| 4,882,168 | 11/1989 | Casey et al. . |
| 4,883,660 | 11/1989 | Blackman et al. . |
| 4,920,203 * | 4/1990 | Tang et al. ........................... 525/409 |
| 4,942,035 | 7/1990 | Churchill et al. . |
| 5,091,171 | 2/1992 | Yu et al. . |
| 5,158,955 | 10/1992 | Gibson et al. . |
| 5,171,264 | 12/1992 | Merrill . |
| 5,194,253 | 3/1993 | Garrido . |
| 5,208,355 | 5/1993 | Scott . |
| 5,219,564 | 6/1993 | Zalipsky et al. . |
| 5,244,665 | 9/1993 | Natraj et al. . |
| 5,258,391 | 11/1993 | Van Scott et al. . |
| 5,312,437 | 5/1994 | Hermes et al. . |
| 5,362,813 * | 11/1994 | Antonelli et al. ..................... 525/286 |
| 5,393,798 | 2/1995 | Weber . |
| 5,466,444 | 11/1995 | Jurgens . |
| 5,498,407 | 3/1996 | Atlas . |
| 5,561,157 | 10/1996 | Yu et al. . |
| 5,610,214 * | 3/1997 | Olson .................................. 524/311 |
| 5,612,052 | 3/1997 | Shalaby . |
| 5,702,688 * | 12/1997 | Yu et al. ............................... 424/59 |

FOREIGN PATENT DOCUMENTS

| | | |
|---|---|---|
| 0 358 528 | 3/1990 | (EP) . |
| WO93/17669 | 9/1993 | (WO) . |
| WO93/24476 | 12/1993 | (WO) . |

OTHER PUBLICATIONS

Ali, et al., "Mechanisms of polymer degradation in implantable devices. 2. Poly(DL–lactic acid)," *J. Biomedical Materials Res.* 27:1409–1418 (1993).

Harris, J.M., "Laboratory Synthesis of Polyethylene Glycol Derivatives," *Rev. Macromol. Chem. Phys.* C25(3):325–373 (1985).

Larock, R.C., "Comprehensive Organic Transformations," New York p. 391 (1989).

Merck Index, 10th ed., Merck & Co., N.J. (1983), at p. ONR–60.

Zalipsky, et. al., "Attachment of Drugs to Polyethylene Glycols," *Eur. Polymer J.* 19:1177–1183, (1983).

* cited by examiner

Primary Examiner—Neil S. Levy
(74) Attorney, Agent, or Firm—Arnall Golden & Gregory, LLP

(57) ABSTRACT

A method for alleviating the symptoms of a cosmetic or dermatologic skin condition is described. An effective amount of a poly(hydroxy acid)/polymer conjugate in a pharmaceutically or cosmetically acceptable vehicle is provided. Topical compositions of the conjugates with another cosmetic or dermatological agent, and compounds of the conjugates having attached physiologically active functional groups, are also provided.

10 Claims, No Drawings

POLY(HYDROXY ACID)/POLYMER CONJUGATES FOR SKIN APPLICATIONS

This is a Divisional of U.S. Ser. No. 08/739,644, filed Oct. 30, 1996, by Arthur J. Coury, Luis Z. Avila, Chandrashekhar P. Pathak, and Shikha P. Barman entitled "HYDROXY-ACID COSMETICS" now U.S. Pat. No. 5,879,688 which is a Divisional of U.S. Ser. No. 08/401,931, filed Mar. 9, 1995, by Arthur J. Coury, Luis Z. Avila, Chandrashekhar P. Pathak, and Shikha P. Barman, for "POLY(HYDROXY ACID)/POLYMER CONJUGATES FOR SKIN APPLICATIONS", now issued as U.S. Pat. No. 5,618,850.

BACKGROUND OF THE INVENTION

This invention relates to poly(hydroxy acid)/polymer conjugate formulations for cosmetic and dermatological skin applications, and methods of use thereof.

Skin disorders range from various cosmetic conditions to severe dermatologic diseases. Conventional treatments for many of these disorders have included topical applications of oils, emollients, humectants, drugs and medicaments. Such treatments have met with varying degrees of success.

It is also known to use hydroxy acids, especially alpha and beta hydroxy acids, in the treatment of various skin conditions, for example, as reviewed in U.S. Pat. Nos. 5,091,171 and 4,363,815 to Yu and Van Scott, which describe the use of various hydroxy acid monomers and oligomers (containing two or three units) in skin treatment. Other patents relating to skin treatment with hydroxy acids include U.S. Pat. Nos. 3,988,470, 4,105,782, 4,234,599,4,380,549, and 5,258,391. Others describing the use of hydroxy acids in skin treatment include EP 0 358 528 by Periera, U.S. Pat. No. 4,294,852 to Wildnauer et al., and U.S. Pat. No. 2,726,982 to Ochs.

While hydroxy acids are well-known in skin treatment, there are various problems inherent in their application to skin, especially from the point of view of safety. In particular, use of a formulation which contain free monomeric hydroxy acids results in an immediate one-time introduction of the full dosage upon application to the skin, which can cause peeling, chemical burning and even scarring of the skin. This problem is specially acute with the more concentrated doses described in the Yu et al patents, referred to above.

In principle, this problem can be overcome by polymerization of the hydroxy acids (HAs) to form polyhydroxy acids (PHAs). Polyhydroxy acids such as polylactic acid, polyglycolic acid, are polycaprolactone are well-known in the manufacture of degradable medical devices, such as sutures (for example, Vicryl®), absorbable sponges and fabrics, and other devices. They are suitable for such uses because PHAs become water-insoluble at relatively low degrees of polymerization. The polyhydroxy acids gradually degrade back to the monomeric acids in the presence of water or of bodily fluids at approximately neutral pH. The principal drawback of these materials is a mild degree of irritation or inflammation at the site during the degradation of the polymer. This is acceptable in the context of wound repair, but is less acceptable in treatment of the skin for relief of cosmetic problems.

Moreover, it is difficult to eliminate this effect by dissolving or dispersing the PHAs in solvent. It is known that polyhydroxy acids such as polyglycolic acid are not soluble in skin-compatible. solvents, but only in organic solvents such as hexafluoroacetone hexahydrate or hexafluoroisopropanol, acetone, and methylene chloride. Attempts to disperse pure PHAs in other components of a cosmetic formulation are thus difficult, and could lead to phase separation of a PHA-rich phase within the formulation, leading to gradations of different concentrations of the hydroxy acid on the skin to which the formulation is applied.

It is therefore an object of the invention to provide a safe, effective and easy method for alleviating the symptoms of a cosmetic or dermatologic skin condition.

It is a further object of the invention to provide a method for the controlled release of hydroxy acids onto the skin of a person to alleviate the symptoms of a cosmetic or dermatologic skin condition.

It is another object of the invention to provide a method for alleviating the symptoms of a cosmetic or dermatologic skin condition which combines the advantages of a humectant and an hydroxy acid.

It is a still further object of the invention to provide a method for alleviating the symptoms of a cosmetic or dermatologic skin condition by providing a formulation which results in substantially uniform application of hydroxy acids to the skin.

SUMMARY OF THE INVENTION

A method for alleviating the symptoms of a cosmetic or dermatologic skin condition is provided wherein an effective amount of a poly(hydroxy acid)/polymer conjugate in a pharmaceutically or cosmetically acceptable vehicle is topically applied to the skin. Vehicles include powders, lotions, gels, sprays, sticks, creams, ointments, liquids, emulsions, foams and aerosols. The conjugate consists of a backbone polymer having poly(hydroxy acids) or derivatives thereof coupled to the backbone to form a brush, linear or branched copolymer. Selection of the backbone can be used to impart desirable properties, as well as control the rate of degradation, and, in turn, the rate of release of hydroxy acids to the skin.

The conjugates can also be used as a method for delivering to the skin a physiologically active functional group, such as a fragrance, an anti-microbial such as a bactericide or fungicide, acne medication, wart remover such as salicylic acid with or without other hydroxy acids, a reductant to bleach skin spots such as hydroxyquinone, a nutrient such as vitamin A or other vitamins, and sunscreens.

DETAILED DESCRIPTION OF THE INVENTION

A method for alleviating the symptoms of a cosmetic or dermatologic skin condition has been developed in which an effective amount of a poly(hydroxy acid)/polymer conjugate in a pharmaceutically or cosmetically acceptable vehicle is topically applied to the skin.

Applications

As used herein, compositions referred to for cosmetic use, skin application, or topical use, encompass treatments and uses which are specifically medicinal as well as conventional cosmetic uses such as in beauty aids and toiletries.

By skin conditions is meant any skin condition whose symptoms can be alleviated by the poly(hydroxy. acid)/polymer conjugates described herein. Examples of skin conditions include dry skin, xerosis, ichthyosis, dandruff, brownish spots, keratoses, melasma, lentigines, age spots, liver spots, pigmented spots, blemishes, wrinkles, skin lines, fine lines, oily skin, acne, warts, eczema, pruritic skin, psoriasis, inflammatory dermatoses, disturbed keratinization, skin changes associated with aging, nail or skin requiring cleansers, conditioners or treatment, and hair or scalp requiring shampooing or conditioning.

Additional uses are associated with application to the skin of antibiotics, antifungals, pediculicides, antiperspirants, antipruritics, analgesics, anesthetics, treatments for blisters, canker sores, insect bites and diaper rash, insect repellents and sunscreens. Preferred uses of the conjugate are for dry skin or wrinkles.

Polymeric Conjugates

As discussed above, the hydroxy acids typically used in medicinal and cosmetic applications are hydroxy acid monomers or polymers of hydroxy acids.

In contrast, as described herein, hydroxy acid conjugates or copolymers have now been found to be advantageous, due to a more defined release rate and avoidance of concentration gradients.

The poly(hydroxy acid)/polymer conjugate may be represented by the formula $$P_aH_b$$

where P is a polymer block having monomer subunits M, in which the monomer subunits are the same or different, and a plurality of which are not hydroxy acids; H is a poly(hydroxy acid) block; and a and b are integers of one or more and denote the number of P and of H blocks in the copolymer. The P blocks and H blocks can be joined in any convenient arrangement. Simple linear arrangements are contemplated, in which the blocks are joined P-H, P-H-P, or H-P-H. The last arrangement, which is a preferred embodiment, is readily made by polymerizing monomeric or dimeric hydroxy acid derivatives, such as lactide, glycolide, or caprolactone, onto a dihydroxy terminated compound such as a polyethylene glycol. Other arrangements of P and H include star copolymers or brush copolymers in which multiple H blocks are dependent from a single P chain, P-H$_b$ where b is greater than 2. The alternative, P$_a$H, where a is greater than two, is generally less preferable, but is possible if one or more of the hydroxy acids comprising block H contains more than one hydroxyl group, as with glyceric acid. Further, the P and H blocks can alternate in a larger polymer, which can be linear or branched—for example, PHPHPH . . . . If a polymer of this sort is desired, it can be made by forming a symmetrical H block by polymerizing a hydroxy acid onto a divalent or multivalent initiator, such as ethylene glycol, glycerol, or erythritol. The resulting H blocks can be crosslinked with an activated P group, for example, isocyanate-terminated polyethylene glycol, to form copolymers useful in the invention.

The monomer subunits of either polymer are most typically in a linear arrangement, but may also be branched. The polymer P may itself be a block, graft or brush copolymer of other polymeric ingredients, the plurality of which are not polyhydroxy acid polymers. P has a total molecular weight of from about 200 to about 200,000 Daltons, preferably from about 400 to 50,000 Daltons, and more preferably from about 500 to about 25,000 Daltons. P has at least one reactive group onto which H blocks can be polymerized or grafted. Any sufficiently reactive group is suitable. Examples of reactive groups are hydroxyl, carboxyl, amine, imine, amide, azide, sulfide, sulfhydryl, sulfate, sulfonate, phosphate, halogen, ester, phenol, acetal, hemiacetal, isocyanate, cyanate, allyl, vinyl, acrylyl, nitro, nitrile, and aldehyde. Other examples of suitable reactive groups will be apparent to those skilled in the art. Preferred reactive groups are hydroxyl, carboxyl, and amine. Hydroxyl is most preferred.

The reactive groups may have their reactivity further enhanced by derivatization with activation reagents appropriate to the chemistry of the group. These are well known in the art; illustrative examples include carbodiimides for activation of carboxyl or amine groups; bisulfites for stabilizing aldehyde groups; aryl disulfide reagents as leaving groups for sulfhydryls; phosgene for amines, alcohols, and phenols; and di-isocyanates for hydroxyls, amines or carboxyls.

The weight fraction of the poly(hydroxy acid) blocks in the poly(hydroxy acid)/polymer conjugate can range from about 1% to as high as at least about 60% by weight, preferably in the range of about 2% to about 40%, and more preferably in the range of about 3% to about 25%. Lower concentrations of hydroxy acid groups will make the conjugate more water-soluble and more easily dispersible; higher concentrations may be more effective per unit weight. The detailed choice of weight concentration of hydroxy acids in the composition will be dictated in part by the exact end use of the conjugate.

The total molecular weight of the conjugate (of poly(hydroxy acid) with backbone polymer) is not critical, and can be varied from about 300 D to over 30 300,000 D. More typical molecular weights are from about 500 to 100,000 D, and in most instances conjugate molecules of from about 1000 to 50,000 D are employed. The viscosity of the polymer is important in giving a cosmetic or therapeutic composition with the correct spreadability and feel for the particular use, and can be controlled by selecting the molecular weight and the relative proportion of the blocks, using established principles.

Backbone Polymers

P may be any polymer which, when grafted or otherwise bonded with H blocks, gives the properties desired in a cosmetic ingredient. These qualities include humectancy; dispersability in cosmetic base ingredients (such as lotions), or ready spreadability on the skin; and non-irritancy of the skin by the polymer P, which may remain on the skin after the hydroxy acids have been liberated to have their effect. Since polymeric hydroxy acids generally have low humectancy, it is desirable that P be a humectant, which implies that P is preferably hydrophilic. Moreover, it is highly preferable that P be a polymer which is approved or Generally Recognized as Safe for application to the skin. Individual examples and lists of such polymers may be found in the literature; in particular, the Cosmetics, Fragrance and Toiletries Dictionary lists most ingredients commonly used in cosmetic formulations. Approved uses of potential cosmetic ingredients can be found in the Merck Index.

Illustrative examples of P include polyethylene. oxide (PEG), also known as polyethylene glycol or polyoxyethylene; polypropylene oxide; copolymers of polyethylene oxide with other alkylene oxides, particularly as block copolymers of PEG and polypropylene oxide or polybutylene oxide (known as Pluronics, Tetronics, or Butyronics, available from BASF); other single-component and mixed polyalkylene oxides; polyvinyl alcohol and partially hydrolyzed polyvinyl acetate; polyvinyl pyrrolidone (Povidone); poylethyloxazoline; polyethyleneimine; polymers based on (meth)acrylates (i.e., acrylates, methacrylates and copolymers thereof), including (meth)acrylic acid, (meth)acrylamides, hydroxyethyl (meth)acrylates such as HEMA, other carboxyl-substituted (meth)acrylate derivatives, copolymers of these, and copolymers of these with other ethylenically unsaturated monomers, including ethylene, maleic acid or maleic anhydride, styrene, and fumaric acid;

mixed copolymers of the monomers of the above materials, for example poly(ethylene-vinyl acetate)(EVAC).

Suitable natural or semi-synthetic polymers include polysaccharides such as starch, cellulose, derivatized celluloses (including hydroxyethyl cellulose, methyl hydroxypropyl cellulose, carboxymethyl cellulose and diethylaminoethyl cellulose), dextran and dextran sulfate, levulan, chitin and chitosan, xanthan, galactomannans such as locust bean gum, gellan, xanthan, schizophyllan, agar, agarose, hydroxyethyl agarose, carrageenan, alginate and propylene glycol alginate, konjac glucomannan, locust bean gum (carob flour), guar, pullulan, schizophyllan, dextrins, maltodextrins, and starches; heparin and related polysaccharides; glycosoaminoglycans such as hyaluronic acid; nucleic acids including DNA and RNA; proteins including gelatin, collagen, albumin, ovalbumin and polyamino acids; peptides; lipids including fatty acids, steroids, phospholipids, lysolipids and fatty acid dimers; and polyphenols, such as tannins; or combinations thereof. In certain embodiments, glycosoaminoglycans other than deacetylated hyaluronic acid are used.

Preferably, P is PEG (polyethylene glycol or polyethylene oxide), polyalkylene oxide, polyvinyl alcohol, polyacrylic derivatives, dextran, hydroxyethylcellulose, starch or combinations thereof.

Most preferably, P is PEG (polyethylene glycol or polyethylene oxide). Among the characteristics that make PEG a preferred polymer are its high hydrophilicity and water solubility, its humectancy, and its excellent biocompatibility.

In certain embodiments, P is a non-amphoteric or non-pseudoamphoteric polymer. By amphoteric is meant a substance that behaves either as an acid or a base, and can be an organic or an inorganic compound. The molecule of an organic amphoteric compound consists of at least one basic and one acidic group. The basic groups include amino, imino and guanido groups. The acidic groups include carboxylic, phosphoric and sulfonic groups. Inorganic amphoteric compounds include certain metallic oxides such as aluminum oxide and zinc oxide. By pseudoamphoteric compounds are meant compounds that are either structurally related to true amphoteric compounds or capable of inducing the same function when they are incorporated into the compositions containing poly(hydroxy acids).

Hydroxy Acids

H represents a block consisting substantially, predominantly or entirely of hydroxy acid monomers. H is preferably formed by the condensation of n hydroxy acid subunits A; H can also be described as $A_n$. The linkages between the hydroxy acid subunits in H will typically be esters. Each of the n hydroxy acid subunits in a given H block may be the same or different. It will typically more convenient in synthesis to make each of the H blocks substantially identical to the other H blocks in composition and length, within the limitation of the statistical nature of many polymerization processes, which will produce random variations about a mean of composition and of chain length.

The number of H blocks in the copolymer is b, which is an integer at least equal to 1, preferably 1 to about 100, more preferably 2 to about 50 or 4 to about 80 depending on application. Larger values of b may require that the values of n, described next, are towards the lower end of the range for n in order to retain the desired balance of activity, spreadability and humectancy.

Hydroxy acids are organic molecules containing at least one carboxylic acid function and at least one hydroxyl group in addition to the carboxyl. Typical hydroxy acids are lactic, glycolic, glyceric and salicylic; as described herein, carbonic acid is defined as an hydroxy acid. Any hydroxy acid which alleviates the symptoms of a cosmetic or dermatologic skin condition can be used. The hydroxy acid can be an alpha, beta, gamma, delta, epsilon or omega hydroxy acid.

Preferred hydroxy acids are any small organic molecule of monomer molecular weight less than about 400 daltons which contains at least one hydroxyl group and at least one carboxyl group. More preferred hydroxy acids contain only one of either a hydroxyl or carboxyl group. Most preferred hydroxy acids contain one hydroxyl and one carboxyl group, such as normal alkanes or alkenes derivatized at the 1-position to form a carboxyl group, and substituted at a carbon atom numbered 2 or greater with an hydroxyl group. Hydroxy acid is also meant to include carbonic acid, which is similar to a 1-hydroxy carboxylic acid. It is preferable that the hydroxy acids contain no amine, sulfur, or other reactive group, besides hydroxyl or carboxyl, unless such other reactive group is blocked or protected.

The hydroxy acid subunits A have the formula (HO)RC(=O)OH, where R is selected from a covalent bond and an alkyl (normal, branched or cyclic), alkenyl or aryl group having from 1 to 25 carbon atoms, preferably 1 to 10, most preferably 1 to 6. R may be further substituted by additional groups, selected from hydroxyl, carboxyl, amide, lower alkyl mono-and di-amide, lower alkyl ester, halogen, sulfate, sulfonate and phosphate, where lower alkyl is a linear or branched alkane or alkene with 1 to 6 carbons and may also contain up to two hydroxyl groups. The additional groups may be connected to R through an ether linkage. It should be noted that under this formula carbonic acid is defined as a hydroxy acid. The obligatory OH (hydroxyl) is joined to the R at any carbon of the R, but preferably at the alpha (or 2-), beta (or 3-) or gamma (4-) positions with respect to the carboxyl. Preferred hydroxy acids are lactic, glycolic, hydroxybutyric, hydroxycaproic and salicylic.

The A subunits are preferably joined by ester linkages. When the subunits each have only one carboxyl and one hydroxyl, the An (i.e., H) block can be represented as

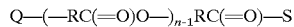

where one of Q and S is a covalent linkage to the backbone polymer P, and the other is selected from a hydroxyl group, a carboxyl group, or a lower alkyl (as defined above) ether or ester, or a polymerizable group or a physiologically active functional group, or a covalent linkage to the same or another backbone polymer P; and where each of the R groups is an R as defined above, and each of the R groups may be the same or different. When one or more of the R contains hydroxyl or carboxyl groups, then the hydroxy acid polymer block An may be branched.

Other linkages may be used besides the ester linkage, as long as the linkage confers the property of slow spontaneous hydrolysis in the presence of water on the linkage. In the particular case when R is a covalent bond, it is convenient to polymerize a cyclic carbonate, such as trimethylenecarbonate, to form a polymer

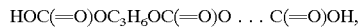

which can be considered as the copolymer of "1-hydroxy carboxylic acid" (carbonic acid) and propane 1,3-diol. Thus, the hydroxy acids may be linked by dihydroxy lower alkyl groups, particularly when R is a covalent bond.

In synthesis of the poly(hydroxy acids), various forms of the hydroxy acids can be used for the polymerization, including free acids, salts, anhydrides or lactones. Preferably, lactones are used, such as the dimeric ring lactones (lactide or glycolide), or lactones such as caprolactone, valerolactone, or butyrolactone.

Lists of potentially suitable hydroxy acids can be found in the literature, for example in various patents by Yu and van Scott. Examples of alkyl alpha hydroxy acids include 2-hydroxyethanoic acid (glycolic acid), 2-hydroxypropanoic acid (lactic acid), 2-methyl 2-hydroxypropanoic acid (methyl lactic acid), 2-hydroxybutanoic acid, 2-hydroxypentanoic acid, 2-hydroxyhexanoic acid, 2-hydroxyheptanoic acid, 2-hydroxyoctanoic acid, 2-hydroxynonanoic acid, 2-hydroxydecanoic acid, 2-hydroxyundecanoic acid, 2-hydroxydodecanoic acid (alpha hydroxylauric acid), 2-hydroxytetradecanoic acid (alpha hydroxymyristic acid), 2-hydroxyhexadecanoic acid (alpha hydroxypalmitic acid), 2-hydroxyoctadecanoic acid (alpha hydroxystearic acid) and 2-hydroxyeicosanoic acid (alpha hydroxyarachidonic acid). Preferred alpha hydroxy acids are glycolic acid and lactic acid.

Examples of aralkyl or-aryl alpha hydroxy acids include 2-phenyl 2-hydroxyethanoic acid (mandelic acid), 2,2-diphenyl 2-hydroxyethanoic acid (benzilic acid), 3-phenyl 2-hydroxypropanoic acid (phenyllactic acid), 2-phenyl 2-methyl 2-hydroxyethanoic acid (atrolactic acid), 2-(4'-hydroxyphenyl) 2-hydroxyethanoic acid, 2-(4'-chlorophenyl) 2-hydroxyethanoic acid, 2-(3'-hydroxy-4'-methoxyphenyl) 2-hydroxyethanoic acid, 2-(4'-hydroxy-3-methoxyphenyl) 2-hydroxyethanoic acid, 3-(2'-hydroxyphenyl) 2-hydroxypropanoic acid, 3-(4'-hydroxyphenyl) 2-hydroxypropanoic and 2-(3',4'-dihydroxyphenyl) 2-hydroxyethanoic acid.

Examples of poly(alpha hydroxy acids) include 2,3-dihydroxypropanoic acid (glyceric acid), 2,3,4-trihydroxybutanoic acid (isomers; erythronic acid, threonic acid), 2,3,4,5-tetrahydroxypentanoic acid (isomers; ribonic acid, arabinoic acid, xylonic acid, lyxonic acid), 2,3,4,5,6-pentahydroxyhexanoic acid, (isomers; allonic acid, altronic acid, gluconic acid, mannoic acid, gulonic acid, idonic acid, galactonic acid, talonic acid), 2,3,4,5,6,7-hexahydroxyheptanoic acid (isomers; glucoheptonic acid, galactoheptonic acid), 2-hydroxypropane-1,3-dioic acid (tartronic acid), 2-hydroxybutane-1,4-dioic acid (malic acid), 2,3-dihydroxybutane-1,4-dioic acid (tartaric acid), 2-hydroxy- 2-carboxypentane-1,5-dioic acid (citric acid), 2,3,4,5-tetrahydroxyhexane-1,6-dioic acid (isomers; saccharic acid, mucic acid). Cyclic hydroxy acids such as salicylic acid and appropriate derivatives can also be used in the conjugates.

Examples of beta hydroxy acids which can form the poly(hydroxy acid) units include hydracrylic acid, 3-hydroxy butyric acid, 3-hydroxy pentanoic acid and 3-hydroxy caproic acid. Preferred beta hydroxy acids are 3-hydroxy-1-alkanoic acids where the alkane is selected from alkanes having about 3 to about 25 carbon atoms, preferably about 3 to about 6 carbon atoms. Salicylic acid may also be considered a beta hydroxy acid.

Examples of gamma hydroxy acids which can form the poly(hydroxy acid) units include 4-hydroxy butyric acid, 4-hydroxy valeric acid (4-hydroxy pentanoic acid), 4-hydroxy isovaleric acid, 4-hydroxy caproic acid, and 4-hydroxy substituted derivatives of higher fatty acids. 4-hydroxy butyric acid, preferably in the lactone form in the poly(hydroxy acid) unit, is preferred. Examples of delta hydroxy acids include 5-hydroxy pentanoic acid, 5-hydroxy caproic acid, and 5-hydroxy substituted derivatives of higher fatty acids. An example of an epsilon hydroxy acid is 6-hydroxycaproic acid, preferably in the lactone form (commonly known as caprolactone), and 6-hydroxy substituted derivatives of higher fatty acids in the poly(hydroxy acid) unit. Further examples of gamma and higher hydroxy acids can be constructed, as known by those skilled in the art, by using the alpha or beta hydroxy acids listed above, adding a gamma or higher hydroxy (if not already present) to a gamma or higher carbon if present, and deleting any alpha or beta hydroxyls as required. Hydroxy derivatives of common fatty acids, such as 9- or 10- hydroxy derivatives of oleic, linoleic or linolenic acids, may also be used.

Polyhydroxy monocarboxylic acids which maybe polymerized into blocks in the conjugates described herein include glyceric, dihydroxybutyric, ascorbic and glucuronic, mannuronic and other hexose and pentose acids. Other suitable hydroxy acids include those containing more than one carboxyl group and at least one hydroxyl, including but not limited to tartronic, hydroxymalonic, malic, citramalic, hydroxyglutaric, tartaric, hydroxyfumaric, hydroxymaleic, dihydroxy maleic, dihydroxy fumaric, dihydroxy tartaric, citric and isocitric.

The poly(hydroxy acids) can be present as pure species, enantiomeric mixtures, or mixtures of different acids. It is preferable that at least a portion, for example, about 5% to about 10%, of the hydroxy acids are alpha or beta hydroxy acids. Preferably, the proportion is about 10% to about 20% more preferably it is about 20% to about 50%, and most preferably about 50% or more, on a molar basis, of the hydroxy acid monomers present in the poly(hydroxy acid)/polymer conjugate.

The Conjugate

The H or $A_n$ poly(hydroxy acid) block is attached to the P polymer to give a poly(hydroxy acid)/polymer conjugate. Preferably, the attachment is a covalent linkage. The particular linkage can be any linkage that preserves the activity of the hydroxy acid. Preferably, such linkages result from reactions with the hydroxy or carboxy termini of the poly (hydroxy acids). Preferred groups on the polymer are hydroxy, carboxy and amine. Examples of linkages include esters, amides, anhydrides, acetals, hydroxamates, carbonates and ureas, and others as noted above.

Preferred linkages are esters and amides. Methods of synthesizing these linkages are well known to those skilled in the art. Such methods can be found, for example, in textbooks of synthetic organic chemistry, compendia such as Beilstein (Beilstein Handbook of Organic Chemistry, pub. Springer-Verlag, Berlin; multivolume.) and "Fieser and Fieser's Reagents for Organic Chemistry" (John Wiley, N.Y.; multivolume).

For reactions in which the polymer backbone is polyethylene glycol, the article by Harris, J. M., Rev. Macromol. Chem. Phys. C25(3):325–373 (1985), is useful. Specific examples of syntheses are illustrated in the Examples below. Preferably, the linkages are hydrolysable in water. Degradation then takes place through the hydrolysis of the linkage, releasing the polymer and the hydroxy acid and its oligomers. As used herein, "degradable" or "biodegradable" refers to spontaneous hydrolysis in the presence of skin or bodily fluids within a finite and predictable period of less than one year. Preferable degradation times are shorter, of the order of months, weeks, and more preferably days or hours.

Block copolymers are known in which poly(hydroxy acid) blocks are attached to backbone polymers. These copolymers will gradually degrade on exposure to water, liberating monomeric hydroxy acid and the original backbone polymer. For example, copolymers containing blocks of polymerized hydroxy acids (PHA) conjugated to PEG (polyethylene glycol, also called polyethylene oxide or polyoxyethylene) are described in U.S. Pat. No. 2,917,410 to Vitalis, for treatment of textile yarns to impart lubricity. U.S. Pat. No. 3,689,531 to Critchfield, et. al. describe plastics made by copolymerization of hydroxy acids with other monomers. U.S. Pat. No. 3,784,585 to Schmitt, et. al. describes PGA (polyglycolic acid) conjugates with various polymers for rendering plastics biodegradable. U.S. Pat. No. 4,857,602 to Casey, et. al. and U.S. Pat. No. 5,312,437 to Hermes, et. al. described PEGPHA (polyethylene oxide-polyhydroxy acid) conjugates for lubrication of sutures.

U.S. Pat. No. 4,882,168 to Casey, et. al. and U.S. Pat. No. 4,526,938 to Churchill, et. al. use PEG-PHA type copolymers for drug delivery. U.S. Pat. No. 4,563,489 to Urist uses unconjugated polylactic acid for drug delivery. U.S. Pat. No. 4,826,945 to Cohn, et. al. describes PEG-PHA conjugates to make absorbable sutures. U.S. Pat. No. 4,942,035 to Churchill, et. al. describe conjugates of PHA with PVA (polyvinyl alcohol). WO 93/17669 by the University of Texas describe block copolymers of PHAs with various non-ionic backbone polymers, including PEGs of various molecular weights, other polyalkylene oxides and mixed polyalkylene oxides (such as Pluronics®, poloxamers and Tetronics™), PVA, poly(ethylene vinylacetate), polyvinylpyrrolidone, dextran, and soluble derivatives of cellulose (such as hydroxyethyl cellulose). These are used as intermediates in the manufacture of photoreactive gelling macromers for use in adhesion prevention and other internal medical conditions responsive to the application of biodegradable gel barriers. These copolymers are soluble in water; by varying the backbone, solubility in other skin-compatible solvents can be obtained.

All of these publications, the teachings of which are incorporated herein by reference, teach methods for making such block copolymers. Methods for conjugating additional groups to the backbone polymer or the PHA/backbone copolymer are also disclosed by WO 93/17669 by the University of Texas and by others, including WO 93/24476 by Clover Consolidated and Zalipsky, et. al., *Eur. Polymer J.* 19, 1177–1183, (1983).

The use of polyethylene glycols in cosmetics is well known; see, for example, U.S. Pat. No. 4,668,430 to Schmolkka, or U.S. Pat. No. 4,883,660 to Blackman et al. The use of more exotic ingredients, such as hyaluronic acid and deoxyribonucleic acid, is also described in U.S. Pat. No. 5,194,253 to Garrido.

In certain embodiments, one or more of the attached poly(hydroxy acid) units is capped with a polymerizable group attached to the terminus of the poly(hydroxy acid). "Polymerizable" means that the group has the capacity to form additional covalent bonds resulting in cross-linking between individual poly(hydroxy acid)/polymer conjugates. Such cross-linking can result in the formation of a gel, for example, a hydrogel. Examples of suitable polymerizable groups include small molecules with double and triple bonds, such as acrylates, (meth)acrylates, fumaric acid, maleic acid, itaconic acid, allyl groups, vinyl groups, acetylenic groups, propargylic acid, (iso)crotonic acid, aconitic acid, citric acid, isocitric acid, cinnamic acid, and other biologically acceptable polymerizable groups, including molecules linkable to the backbone polymer which carry one or more of such polymerizable groups. Preferably, acrylate-type molecules are used in which cross-linking results from carbon-carbon double bonds. The cross-link density can be varied by variations in the polymer molecular weight, thereby affecting the properties of the gel. A preferred conjugate is acrylated PEG lactate.

The gel can be polymerized by photopolymerization or chemical polymerization. Photopolymerization is characteristically initiated by free radical formation, resulting from photon absorption of certain dyes and chemical compounds to ultimately produce free radicals. The conjugates are polymerized by exposure of the polymerizable regions to the generated free radicals. For example, acrylates can be polymerized using several initiating systems, for example, Eosin dye, by brief exposure to ultraviolet, long wavelength, or visible light.

Useful photoinitiators are those which can be used to initiate by free radical generation polymerization of the conjugates without cytotoxicity and within a short time frame, preferably within minutes, and most preferably within seconds. Preferred dyes as initiators of choice for long wavelength ultraviolet or visible light initiation are ethyl Eosin, 2,2-dimethoxy-2-phenyl acetophenone, other acetophenone derivatives, and camphorquinone. Cross-linking and polymerization are initiated among conjugates by a light-activated free-radical polymerization initiator such as 2,2-dimethoxy-2-phenylacetophenone or a combination of ethyl Eosin ($10^{-1}$ to $10^{-2}$ M) and triethanol amine (0.001 to 0.1 M), for example.

The choice of the photoinitiator is largely dependent on the photopolymerizable regions. When the conjugate includes at least one carbon-carbon double bond, light absorption by the dye causes the dye to assume an excited state, such as a the triplet state or anion radical. The excited molecule subsequently reacts with the amine to form a free radical which initiates polymerization. Using such initiators, copolymers may be polymerized in situ ultraviolet light or by visible light. Initiation of polymerization is accomplished by irradiation with light at a wavelength of between about 200–700 nm, preferably in the long wavelength ultraviolet range or visible range, 320 nm or higher, most preferably about 514 nm or 365 nm.

There are several photo-oxidizable and photo-reducible dyes that may be used to initiate polymerization. These include acridine dyes, e.g., acriblarine, thiazine dyes such as thionine, xanthine dyes such as rose bengal, and phenazine dyes such as methylene blue. These are used with co-catalyst such as amines, including triethanolamine, sulfur compounds including $RSO_2R^1$, heterocycles including imidazole, enolates, organometallics, and other compounds, including N-phenyl glycine. Other initiators include camphorquinones and acetophenone derivatives.

Thermal polymerization initiator systems may all so be used. Such systems are unstable at 37° C. and initiate free radical polymerization at physiological temperatures. Examples include potassium persulfate, with or without tetramethyl ethylenediamine, benzoyl peroxide, with or without triethanolamine, and ammonium persulfate with sodium bisulfite. Azo compounds are also used.

Other initiation chemistries may be used besides free radical initiation. These include water and amine initiation schemes with isocyanate or isothiocyanate containing conjugates used as the polymerizable regions.

A bioerodable hydrogel can be formed, for example, by photopolymerization of aqueous solutions of the poly (hydroxy acid)/polymer conjugates. If the polymer in the conjugates is PEG, preferably the PEG component should be greater than about 40%. by weight to provide dispersability on the skin, especially in water-based formulations.

Polymerization of the end-capped conjugates can occur prior to their application to the skin, or can occur on the skin itself from a solution so as to form a "mask" on the skin.

The chemical cross-links within the gel are preferably attached to hydrolyticly labile groups, so that the gel can degrade into water-soluble products, as described in WO 93/1766 by the University of Texas, Tables 6 and 9. For example, if the conjugate includes PEG which is reacted at its termini with glycolide to form poly(glycolic acid), and end-capped at all poly(glycolic acid) termini with a polymerizable acrylate group, and the conjugate is gelled, the resulting gel is hydrolytically labile via hydrolysis of the poly(glycolic acid) links. Such a gel will degrade into water-soluble non-toxic products, chiefly PEG, glycolic acid and its oligomers, and oligomers of acrylic acid. The degradation rates of the gels can be tailored by appropriate choice of the poly(hydroxy acid) such that degradation is substantially completed in times ranging from hours to several months. Shorter times, in the range of hours to days, will often be preferred in cosmetic applications.

The factors for such tailoring are known to those skilled in the art and are readily adapted to produce the desired rate of hydrolysis. Important factors are that esters involving alpha-hydroxy acids generally degrade faster than esters with beta hydroxy acids, which in turn are faster than esters with more distantly-substituted acids. This result is a consequence of the increasing hydrophobicity of more distantly substituted acids on the ester bond. Similar shifts are seen when substituting other electron-withdrawing groups at the alpha, beta and more distant positions. A second design factor is that the ester or other linkages degrade faster in the amorphous state, and slower in the crystalline state, due to the ease of access to the bond by water molecules. Crystallinity is increased by use of an enantiometrically-pure, single hydroxy acid, such as glycolic acid or L-lactic acid, and decreased by mixtures, such as D,L-lactic acid. A third factor is pH, with degradation occurring faster at higher pH or at pH's below about 3. Thus, buffering the composition containing the polymer to a particular pH in the skin-acceptable range, between about pH 4 and about pH 9, has a significant effect on the degradation rate of the hydroxy acid linkages. The rate of degradation can also be influenced by certain conditions of the skin. See, for example, Ali et al., J. Biomedical Materials Res. 27:1409–1418 (1993).

Degradation time should be tailored to the intended application. For example, in wart removal, it is preferable to expose the wart to hydroxy acid over a period of days to weeks. Extended periods may also be preferred, for example, for lightening of age spots. If covered with a dressing to prevent removal of the poly(hydroxy acid)/polymer conjugate, a conjugate degrading over a period of about a week to about two weeks may be appropriate for these uses. A preferred hydroxy acid for incorporation in a conjugate formulation for the latter use is salicylic acid. An alternative hydroxy ac-id for slow delivery could be enantiometrically pure, such as glycolic acid, with a preferred pH is about pH 6 to about pH 7. For other applications, for example, to reduce the appearance of wrinkles, it is preferable to expose the wrinkles to hydroxy acid for less than about a day. A preferred formulation for this use is D,L-lactic acid, at a slightly alkaline pH, about 7 to about 8. Since the rate of hydrolysis can also be affected by other components in the formulation, some tailoring of the conjugate composition to the overall formulation is also preferable. A controlled release of the hydroxy acids from the poly(hydroxy acid)/polymer conjugates can thus be obtained when the conjugate contacts the skin.

Other Components for Delivery

Other embodiments include attachment of a physiologically active functional molecule or group to an end group, such as to an hydroxy or carboxy end group of the poly (hydroxy acid)/polymer conjugate. In certain embodiments, the conjugate has a plurality of hydroxy end groups, and a physiologically active functional group is attached to at least one of the hydroxy end groups and additionally a polymerizable group, such as acrylate, is attached to at least one of the other hydroxy end groups. Examples of physiologically active functional groups include fragrances, anti-microbials, including bactericides and fungicides, acne medication, wart removers including salicylic acid with or without other hydroxy acids, reductants to bleach skin spots such as hydroxyquinone, nutrients such as vitamin A, retinoic acid (Retin A) or other vitamins, dyes and sunscreens. Preferred functional molecules or groups are retinoic acid (Retin A), or other vitamin A derivatives or precursors. A preferred poly(hydroxy acid)/polymer conjugate to which the physiologically active functional group is attached is PEG-lactate-diol.

It may be synthetically useful to attach a physiologically active functional group through linkages other than those preferred for use in coupling hydroxy acids, including hydroxyls and carboxyls. In such cases, a double-bond functionality on the polymer can be directly linked with an active derivative, or chemically modified to produce such a linking group, taking advantage of the specific functionalities of unsaturated groups. See, for example, Larock, R. C., "Comprehensive Organic Transformations," New York (1989), at 391. For example, primary and secondary amines can be added to double bonds. For example, the Michael reaction allows the addition of an active carbanion across a double bond. See, for example, Merck Index, 10th ed., Merck & Co., N.J. (1983), at p. ONR-60.

The poly(hydroxy acid)/polymer conjugate can have an attached physiologically active functional group. The poly (hydroxy acid)/polymer conjugates and the physiologically active functional groups include those discussed above. The physiologically active functional group is preferably attached to the conjugate. by a covalent linkage, which is preferably (but not necessarily) spontaneously hydrolyzing on the skin to release the active group. In preferred embodiments, the conjugate has at least one hydroxy end group and the physiologically active functional group is attached to at least one of the hydroxy end groups. In certain embodiments, the conjugate has a polymerizable group attached to the terminus of one or more of the $A_n$ units of the conjugate so as to permit cross-linking between individual poly(hydroxy acid)/polymer conjugates. Preferably, the polymerizable groups are cross-linked so as to form a gel, especially during or after application to the skin. In other embodiments, some or all of the polymerizable groups are used to attach physiologically active functional groups to the conjugate.

Topical Compositions of Conjugate and Carrier

In most uses, the conjugate will be dispersed in a cosmetic or therapeutic vehicle. For example, topical cosmetic compositions will include an effective amount of the poly (hydroxy acid)/polymer conjugate and a cosmetic agent in a cosmetically acceptable vehicle. When applied to skin, the requisite amounts of material will depend on the type of application, the duration desired for the effect, and on any compensation required for penetration into the upper layers of the skin, or the degree of abrasion and shedding of the skin.

The conjugate will be present in the overall formulation in amounts from about 0.1% to about 100% by weight, depending on the use of the formulation. In most uses, ranges from about 1% to about 80% are preferred, and ranges from about 2% to about 50% are more preferred. In those uses which require high proportions of hydroxy acid, essentially pure conjugate, preferably diluted with a few percent of stabilizers, buffers or other ingredients regulating hydrolysis, are preferred. The conjugates can be end-capped with a polymerizable group, or with a biologically active group.

The conjugates can be in gel form. Preferably, the pH of the formulation when applied to the skin is in the range of about 4.0 to about 9.0, and more preferably is about 5.0 to about 8.5. Preferably, the dosage form is such that it does not substantially deleteriously affect the person.

A pharmaceutically or cosmetically acceptable vehicle can include a powder, lotion, gel, spray, stick, cream, ointment, liquid, emulsion, foam or aerosol. The poly (hydroxy acid)/polymer conjugate can be incorporated into a liquid in dissolved form or colloidal form. The liquid can be a solvent, partial solvent or non-solvent. In many cases an organic liquid can be used. Preferred solvents or dispersants do not attack the labile ester bonds of the poly(hydroxy acid) during storage. It is therefore preferred that the composition be substantially anhydrous during storage, although water and aqueous solutions may be mixed with the active copolymers shortly before application to the skin.

The conjugate can be applied as a powder. It can be applied as a dry powder to moist skin, or as a premoistened powder to dry skin. Preferably, the resultant paste or solution is allowed to dry to form an essentially invisible skin coating. Over a period of time, as discussed above, the linked poly(hydroxy acid) units gradually hydrolyze to provide hydroxy acids to the skin. Thus, a controlled release of the hydroxy acids from the conjugate can be obtained when the conjugate contacts the skin. The solid formulations containing conjugates also allow for a substantially uniform application of the hydroxy acids to the skin, and prevent phase separation of various components which can occur in formulations which contain polymeric hydroxy acids not conjugated to a backbone polymer.

The composition can include any solid, semi-solid or liquid cosmetically and/or physiologically acceptable vehicle, to enable the copolymer to be conveyed to the skin at an appropriate dilution. The nature of the vehicle will depend upon the method chosen for topical administration of the composition.

The vehicle can itself be inert or it can possess physiological or pharmaceutical benefits of its own. The selection of a vehicle depends on the required product form of the composition. Suitable vehicles can be classified as described herinafter.

Examples of cosmetic agents include emollients, humectants, colorants, pigments, fragrances, moisturizers, viscosity modifiers and any other conventional cosmetic forming agent. One or more cosmetic agents can be included in the cosmetic composition. The form of the cosmetic composition can be a powder, lotion, gel, spray, stick, cream, ointment, liquid, emulsion, foam or aerosol. Lists of such materials, and formulations for the creation of particular types of lotions, creams, sunscreens, lipsticks, and other such forms are widely available in the patent literature and in commercial handbooks, and can be used by those skilled in the preparation of such formulations to incorporate the block copolymer conjugates described herein. A comprehensive list of ingredients approved or customary for use in cosmetics, toiletries and topical medications is given in the *International Cosmetic Ingredient Dictionary*, Fifth Edition, Vols. 1 & 2, ed. J. A. Wenninger; pub.

The Cosmetics, Toiletry and Fragrance Ass'n., Washington, DC 20036-4702. Formulation ingredients used with the copolymers will normally be selected from these ingredients.

To demonstrate the availability of such information, lists of formulation ingredients have been abstracted below from several patents, U.S. Pat. Nos. 4,673,571; 5,158,955; 5,208,355; and 5,244,665; modified as appropriate for use with the conjugates described herein.

The ingredients which are usually present in cosmetic compositions include perfumes, coloring agents, pigments, preserving agents, thickening agents, sequestering agents, emulsifying agents, sun filters, fillers, and stabilizing agents. Compositions can also contain various active substances such as humectant agents and healing agents. Compositions include treatment creams or lotions for the hands or the face, sunscreen creams, tinted creams, make-up removal milks, foamy liquids for baths, after shave lotions, "eau de toilette", shaving foam, pencils for blush, pencils that may be colored especially for lips, for make-up or for body hygiene or for deodorant compositions.

In listing various classes of materials below by function, it is noted that individual ingredients may be useful in more than one functional class, and that there is some overlap between classes (for example, liquid vehicles with emollients, or humectants with surfactants).

Liquid vehicles

Compositions can include at least one cosmetically acceptable vehicle other than water. Vehicles other than water include solids or liquids such as emollients, solvents, humectants, thickeners and powders. Suitable liquid vehicles include mineral oil, silicone oil, lipids (such as lecithin, vegetable oil, vitamin E, and derivatives of lanolin), low-molecular weight glycols such as PEG-4, PEG-6, propylene glycol, glycerine, and their lower alkyl conjugates, and ketones, such as acetone. Solvents containing unconjugated hydroxyls may undergo slow exchange with the ester groups of the polyhydroxy acids; this may affect the bulk consistency of the preparation, but would still result in slow release of the hydroxy acid monomers. Solvents include ethyl alcohol, isopropanol, ethylene glycol monoethyl ether, diethylene glycol monobutyl ether, diethylene glycol monoethyl ether, and acetone.

Humectants

Humectants include glycerin, sorbitol, sodium 2-pyrrolidone-5-carboxylate, soluble collagen, dibutyl phthalate, gelatin, and poly(alkylene oxide)s, such as polyethylene glycol.

Powders

Powders useful alone in dry compositions or as fillers in liquid compositions include chalk, talc, fullers earth, kaolin, starch, gums, colloidal silicon dioxide, sodium polyacrylate, tetra alkyl and/or trialkyl aryl ammonium silicate, organically modified montmorillonite clay, hydrated aluminum silicate, fumed silica, carboxyvinyl polymer, and sodium carboxymethyl cellulose.

Creams

Creams can be made with a support that is a soap-based or fatty alcohol-based formula in the presence of an emulsifier. The soaps can be any known in the cosmetic formulation art, and include natural fatty or synthetic acids having from 12 to 20 carbon atoms (such as lauric acid, myristic acid, palmitic acid, oleic acid, stearic acid and their mixtures) in concentrations of from 10 to 30% neutralized with cosmetically acceptable salts including sodium, potassium, ammonia, monoethanolamine, triethanolamine and their mixtures.

Gels

Cosmetic gels may contain thickening or gelling agents such as sodium alginate or arabic gum or cellulose derivatives optionally in the presence of a solvent. The thickening agent concentration ranges from 0.5 to 30 weight percent and preferably ranges from 0.5 to 15 weight percent. Solvents used can be aliphatic lower alcohols, glycols and their ethers with the concentration of the solvents ranging from 2 to 20%.

Emollients

Emollients include stearyl alcohol, glyceryl monostearate, propane-1,2-diol, butane-1,3-diol, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, polydimethylsiloxane, di-n-butyl sebacate, isopropyl myristate, isopropyl palmitate, isopropyl stearate, butyl stearate, polyethylene glycol, triethylene glycol, lanolin, sesame oil, coconut oil, arachis oil, acetylated lanolin alcohols, petroleum, mineral oil, butyl myristate, isostearic acid, palmitic acid, isopropyl linoleate, lauryl lactate, myristyl lactate, decyl oleate, myristyl myristate.

Spray Propellants

Spray compositions may require propellants, including propane, butane, isobutane, carbon dioxide, and nitrous oxide.

Fragrances

The composition can also include a perfume in an amount sufficient to make the composition acceptable to the consumer and pleasant to use. Usually, the perfume will form from 0.01% to 10% by weight of the composition.

Surface Active Agents

Surface active agents (detergents) useful in cosmetic compositions include anionic surface active agents, such as salts of fatty acids (for example, sodium laurate and triethanolamine oleate), alkyl benzene sulfonates (such as triethanolamine dodecyl benzene sulfonate), alkyl sulfates such as sodium lauryl sulfate, alkyl ether sulfates, monoglyceride sulfates, isethionates, methyl taurides, acylsarcosinates, acyl peptides, acyl lactylates, polyalkoxylated ether glycollates, for example trideceth-7 carboxylic acid, and phosphates such as sodium dilauryl phosphate. Amphoteric surface active agents include imidazole compounds, N-alkyl amino acids, (such as sodium cocaminopropionate and asparagine derivatives), and betaines. Nonionic surface active agents, such as fatty acid alkanolamides, for example, oleic ethanolamide; esters of polyalcohols, for example Span; polyglycerol esters; polyalkoxylated derivatives, for example TRITON X-100™, polyoxyethylene lauryl ether, and TWEEN™; and amine oxides, such as dodecyl dimethyl amine oxides. Cationic surface active agents may be of use in the composition. Mixtures of two or more of the above surface active agents can be employed in the composition. As noted above, many surfactants may also be used for their functionality as emollients, humectants or vehicles.

Sunscreen and Oxidation Resistance

The composition may include an effective amount of a sunscreen agent to provide protection from the harmful effects of excessive exposure to sunlight. This can be particularly important when the skin is partially debrided by the application of a hydroxy acid.

Examples of suitable organic sunscreens, when required, include Benzophenone-3, DEA Methoxycinnamate, Ethyl dihydroxypropyl PABA, Glyceryl PABA, Octyl methoxycinnamate, Octyl salicylate, 2-Phenylbenzimidazole-5-sulfonic acid, and Butyl methoxy dibenzoylmethane. An inorganic sunscreen, such as titanium dioxide or zinc oxide, can also be used. The sunscreen ingredients may be present free in the formulation. The organic sunscreens may also be coupled to the conjugate block copolymer, as described above.

Anti-aging Additives

The composition can also include an additional anti-aging active such as retinol (Vitamin A) and/or derivative thereof, to enhance repair of photodamage to skin following exposure to ultra-violet light. In addition to retinol itself, examples of derivatives of retinol include: Retinyl acetate, Retinyl butyrate, Retinyl propionate, Retinyl octanoate, Retinyl laurate, Retinyl palmitate, Retinyl oleate, and Retinyl linoleate. The amount of retinol, or a cosmetically acceptable derivative thereof, when present in the composition is from 0.01 to 10% and preferably 0.1 to 5% by weight of the composition. The retinols or derivatives may be coupled to the conjugate.

Oxidation Inhibitors

The composition can also include a tocopherol (vitamin E group) as an additive or as an antioxidant for retinol, or a derivative, when present in the composition, and to limit oxidative damage to skin. The vitamin E group includes alpha-tocopherol, beta-tocopherol, gamma-tocopherol, and delta-tocopherol. The amount of tocopherol, when present in the composition, is from 0.0001 to 50%, preferably from 0.001 to 10% by weight of the composition. The tocopherol may be coupled to the conjugate.

Pigments

Pigments are frequently added to cosmetic formulations to achieve a desired color for application to the skin. Such pigments are known and the concentrations required to achieve a desired coloring are readily determinable. Pigments may be inorganic or organic. Inorganic pigments include iron oxides (red, black, brown colors), manganese violet, ultramarines (green, blue, pink, red, or violet aluminum sulfosilicates), aquamarines, copper powder, mica, clays, silica, and titanium dioxide. Organic dyes that have been certified by the US FDA for cosmetic use generally have the prefix "D&C" and a suffix of a color and a number (for example, D&C Green #3). There are at least 27 D&C dyes, each of which may be present as a "lake", i.e., a salt of the dye with aluminum, zirconium, strontium, barium, calcium, potassium or other metallic cations, to produce increased adherence to a substrate. In Europe, many of the same colorants, and additional colorants not approved in the U.S., are listed as "CI" dyes; for example, CI 61570 is chemically the same as D&C Green #5. Each of these pigments may further have several different trade names, or be present in mixed compositions.

Other Additives

The composition can also contain adjuncts other than those already mentioned, depending on the form of the intended product. It is, for example, possible to include antiseptics, preservatives, and coloring agents, which can improve the stability and consumer appeal of the composition. Examples of other materials discussed above include anti-microbials including bactericides and fungicides, acne medication, and wart removers including salicylic acid. Agents known in the art for treatments of conditions such as blisters, insect bites, diaper rash and canker sores may be included; these may be include local anesthetics, emollients, and other known materials.

Preservation of the Composition

Examples of methods that can be employed to achieve preservation of the composition include sterilization (for example, by filtration or heat treatment); addition of chemical preservatives (such as ethanol, benzoic acid, sodium benzoate, sorbic acid, potassium sorbate, sodium propionate and the methyl, ethyl, propyl and butyl esters of p-hydroxybenzoic acid), generally be from 0.05 to 5% preferably from 0.1 to 2% by weight; and water activity depression, as by including glycerol, propylene glycol, polyethylene glycol, sorbitol, sugars and salts, sufficient to reduce the water activity from 1 to less than 0.9, preferably to less than 0.85 and most preferably less than 0.8.

Administration of the Conjugate Formulation

The poly(hydroxy acid)/polymer conjugates is topically applied. The conjugates can be administered prior to or subsequent to appearance of the skin condition. In certain embodiments, the conjugates are administered to persons who have reached a particular age and who therefore are more likely to develop one of the skin conditions. In other embodiments, the conjugates are administered to persons who exhibit either early or advanced symptoms of the skin condition.

The poly(hydroxy acid)/polymer conjugates are administered in an effective amount. Examples of alleviating the symptoms of the skin conditions referred to above include treating the condition, curing the condition, reducing the appearance of the condition, improving the appearance of the condition, creating a pleasing sensation on the skin, modifying the symptoms of the condition, preventing the condition or preventing worsening of the condition. An effective amount can be determined on an individual basis and will be based, at least in part, on consideration of the particular skin condition, on the severity of the particular skin condition, on the age of the person receiving the application, on the skin sensitivity of the particular person receiving the application, on the particular poly(hydroxy acid)/polymer conjugate used, on the rate of degradation of the conjugate used, on the vehicle in which the conjugate is in, and on the dose regimen that is employed. An effective amount can be determined by one of ordinary skill in the art employing such factors and using no more than routine experimentation.

For example, for topical application of acrylated-capped PEG-polylactate conjugates to wrinkled skin, the formulation in a cream form (10% poly(lactate) by weight) is applied to the wrinkled area of skin on a person. It is then gelled via an included initiator with visible or long-wavelength UV light. The resulting gel "mask" is allowed to remain in place for one to four hours, after which it is removed. Topical application, one time daily, is continued for four weeks. The skin shows reduction in the appearance of wrinkles. Similar advantageous results are obtainable with other poly(hydroxy acid) /polymer conjugates.

In another example, acrylated capped PEG-poly(glycolic acid) conjugates having attached hydroxyquinone groups may be topically applied to skin to bleach skin spots. A composition of the conjugates in powder form (6% poly (glycolic acid) by weight) is applied to the area of skin on a person which has skin spots, two times daily, for three weeks. Similar results are obtainable with other poly (hydroxy acid)/polymer conjugates, and with other forms of the composition.

Similar beneficial results are obtainable when the formulation is applied to alleviate the symptoms of dry skin, xerosis, ichthyosis, dandruff, keratoses, melasma, lentigines, blemishes, wrinkles, skin lines, fine lines, oily skin, acne, warts, eczema, pruritic skin, psoriasis, inflammatory dermatoses, disturbed keratinization, brownish spots, age spots, liver spots, pigmented spots, and skin changes associated with aging.

Product Form and Container

The compositions can be formulated as liquids, for example as a lotion, shampoo, milk or cream for use in conjunction with an applicator such as a roll-ball applicator, a spray device such as an aerosol can containing propellant, or a container fitted with a pump to dispense the liquid product. For example, a topical skin treatment composition can be formulated as a lotion having a viscosity of from 4,000 to 10,000 mPas, a fluid cream having a viscosity of from 10,000 to 20,000 mPas or a cream having a viscosity of from 30 20,000 to 100,000 mPas, or above. The composition can be packaged in a suitable container to suit its viscosity and intended use by the customer. Alternatively, the compositions of the invention can be solid or semi-solid, for example sticks, powders, creams or gels, for use in conjunction with a suitable applicator or simply a tube, bottle, or lidded jar, or as a liquid-impregnated fabric, such as a tissue wipe.

EXAMPLES

The present invention will be further understood by reference to the following non-limiting examples of the conjugates and conjugate formulations for topical and cosmetic applications.

Example 1
Synthesis of PEG-Polylactate Conjugates.

This example illustrates the synthesis of PEG-polylactate conjugates. 1 kg of water-soluble polyethylene glycol (PEG), MW 8 K, was azeotropically dried by dissolving the polymer in toluene and distilling off the toluene-water azeotrope under a positive stream of inert gas. The resultant dried solution was cooled to approximately 80° C. and 53.2 g of D,L-lactide was charged to the reaction flask. The resultant hot reaction mixture was reheated to boiling and additional toluene was distilled off to remove any residual water via the azeotrope. The reaction was refluxed for approximately 16 hrs and subsequently cooled to approximately 50° C. This warm toluene solution was poured into hexane to precipitate PEG-lactate-diol (PLD), which was collected via filtration, washed with fresh hexane and mostly dried on the filter with a sufficient stream of inert gas. The damp powder was dried to a constant weight at 40° C. in a vacuum oven.

Example 2
Synthesis of Capped PEG-Polylactate Conjugates By Acrylation.

This example illustrates the synthesis of PEG-polylactate conjugates capped by acrylation. Solvent-wet PEG-lactate-diol (PLD) prepared as in Example 1 was azeotropically dried by redissolving in toluene and distilling off the toluene-water azeotrope under a positive stream of an inert gas. The dry toluene solution of PLD was cooled to approximately 55° C. and 46.2 g of distilled triethylamine and 25.3 g of distilled acryloyl chloride were added, respectively. After reacting for approximately 20 min at approximately 50° C., the resultant mixture was filtered warm at approximately 40° C. through a medium porosity sintered glass funnel to remove most of the byproduct salts. The still-warm filtrate was poured into hexane to precipitate the crude acrylated PLD, which was collected via filtration, washed with fresh hexane, and then mostly dried on the filter with a sufficient stream of inert gas. The slightly toluene-wet crude acrylated PLD together with a protective amount of hydroquinone (about 25 ppm) was dissolved in fresh warm (approximately 40° C.) toluene, filtered again to remove residual salts and rapidly passed through a 400 g column of neutral alumina to remove unreacted lactide and other process impurities. A small toluene wash was employed and the entire column eluant was collected together with a small amount (about 150 ppm) of added hydroquinone, which dissolves on warming. This solution was poured into hexane to precipitate a nearly colorless solid, which was collected via filtration, washed with fresh hexane, and subsequently dried under vacuum at approximately 40° C. to a constant weight to yield approximately 900 g of purified acrylated PLD, containing a small amount of hydroquinone. The acrylated PLD was found to contain on average about 3.7±0.5 lactate groups on each end of the molecule.

Example 3
Crosslinking of Acrylated Capped PEG5 Polylactate Conjugates.

This example illustrates cross-linking by photopolymerization of the acrylated capped PEG-polylactate conjugates prepared in Example 2. The conjugates were gelled by photopolymerization using free radical initiators, with the presence of two acrylic double bonds per chain leading to rapid gelation. A 23% w/w solution of the conjugates in HEPES buffered saline containing 3 ml of initiator solution (300 mg/ml of 2,2-dimethoxy-2- phenyl-acetophenone in N-vinyl pyrrolidone) was used. 100 microliters of the solution were placed on a glass coverslip and irradiated with a low intensity long wavelength UV (LWUV) lamp (Blak-Ray, model 3-100A with flood). The time required for gelation to occur was approximately 10 seconds.

Example 4
Synthesis of PEG-Lactate and PEG-Lactate Acrylate From High Molecular Weight PEG.

This example illustrates the synthesis of high molecular weight PEG-lactate diol and PEG-lactate acrylate. 40 gm of PEG (MW 20,000) and 0.865 g of D,L-lactide were coupled as in Example 1. 30 gm of the product was acrylated with 0.299 g triethanolamine and 0.268 g acrylic acid as in Example 2.

Example 5
Synthesis of PEG-Lactate Diol From Low Molecular Weight PEG.

This example illustrates the synthesis of low molecular weight PEG-lactate diol. 60 g of PEG-600 NF (MW 600; Union Carbide) was esterified with 24 g of lactide in the presence of 0.338 g stannous octanoate in the molten state after azeotropic drying with 50 ml of toluene. The oily product was recovered from hexane, dissolved in toluene, reprecipitated with hexane, and dried in a round bottom flask under vacuum.

Example 6
Synthesis and characterization of F127-(Lactate)-OH, Lactyl D.P. 10.91.

This example illustrates the synthesis and characterization of F127-(lactate)-OH. 100 g of Pluronic™ F127 poloxamer (BASF) were charged in a 250 ml Schlenk apparatus and melt dried at 100° C. under vacuum for at least 4 hours. 22.86 g of D,L, lactide (Boehringer Ingelheim, Lot #27689) were added to the melt under a nitrogen atmosphere at 170° C. followed by addition of 0.5 mole % stannous 2-ethylhexanoate (Sigma) to obtain a 200:1 monomer: catalys ratio. The reaction temperature was maintained between 170–180° C. under nitrogen for 4 hours. The reaction product melt was allowed to cool to 100° C., then diluted with a 200 ml addition of anhydrous toluene. The cooled reaction mixture was precipitated in a large excess of hexane (EM Sciences), collected on a coarse filter and dried to constant weight under vacuum at 40° C. Yield: 85 g. The degree of lactyl substitution was 10.91 by NMR. The viscosity of a 10% (w/v) aqueous solution was 14.98 centipoises.

Example 7
Synthesis of PEG-Lactate-Cinnamate.

This example illustrates the synthesis of PEG-lactate conjugates attached to cinnamate, which can be used as a sunscreen.

(I) Synthesis of PEG-Lactate-Diol with Lactate D.P. of 4–5

100 g of polyethylene glycol (MW 8000; Union Carbide, Lot #1s 596679) were charged in a 250 ml Schlenk apparatus and melt dried at 100° C. under vacuum for at least 4 hours. 18.0 g of D,L, lactide (Boehringer Ingelheim, Lot #27689) were added to the melt under a nitrogen atmosphere at 170° C. followed by addition of 0.5 mole % stannous 2-ethylhexanoate (Sigma, Lot #1554) to obtain a 200:1 ratio of monomer to catalyst. The reaction temperature was maintained between 150–180° C. under nitrogen for 4 hours. The reaction product melt was allowed to cool to 100° C., then diluted with a 200 ml addition of anhydrous toluene (Aldrich; water content less than 0.0005%). The cooled reaction mixture was precipitated in a large excess of hexane (Omnisolv; EM Sciences), collected on a coarse filter and dried to constant weight under vacuum at 40° C. Yield: 96 g.

(II) Synthesis of PEG Lactate Cinnamate 95 g of PEG-lactate diol were dissolved in 900 mls of anhydrous toluene (Aldrich, Lot #5114) under a nitrogen blanket at 110° C. 150 mls of toluene were distilled to remove, as the azeotrope, all traces of water from the reaction mixture. The reaction mixture was cooled to 65° C. under a nitrogen flush. Redistilled triethylamine (Amresco, Lot #9078) was added dropwise to the reaction mixture (6.958 ml, a 3× molar excess). 11.464 g (3 molar excess) of cinnamoyl chloride (Aldrich, Lot #67891) were added under a nitrogen flush. The reaction mixture turns turbid yellow with the formation of triethylamine hydrochloride. The reaction mixture was stirred at 65° C. under nitrogen for 12 hours. The hot reaction mixture was filtered through a 10–15 M porosity sintered glass funnel, and precipitated in a 10 volume excess of hexane (EM Sciences). The crude product was collected on a 40–60 porosity sintered glass funnel.

The crude product was redissolved in THF (EM Sciences) at 50° C., and filtered through a 10–15 M porosity filter. The filtrate was purified by passing through a packed alumina bed filter (100 g). The clear filtrate was precipitated in a 10 volume excess of hexane (EM Sciences), collected by filtration, and dried in vacuum at 40° C.

Characterization of Cinnamate Derivatives
Yield: 81.6 g dry weight
Lactyl D.P.: 3.98 (NMR, IC)
Cinnamyl D.P.: 2.15 (nominal) (NMR)
Viscosity (10% w/w in deionized water): 13.23
Centipoise: Brookfield Viscometer Model 201
UV-Vis Spectroscopy $I_{max}$=275 nm: Nicolet UV-Vis Spectrometer 2.0
Critical Micellar Concentration: 4.34% in deionized water: UV-Vis Spectrometer, Nicolet; Wyatt Dawn Light Scattering Spectrophotometer.

Example 8
Synthesis and Characterization of PEG-Trimethylene Carbonate Conjugates.

This example illustrates the synthesis and characterization of PEG-trimethylene carbonate conjugates. 100 g of polyethylene glycol (MW 8000; Union Carbide, Lot #1s596679) were charged to a 250 ml Schlenk apparatus and melt dried at 100° C. under vacuum for at least 4 hours. 9.358 g of trimethylene carbonate (Boehringer Ingelheim, Lot #81567) were added to the melt under a nitrogen atmosphere at 180°

C. followed by addition of 0.5 mole % (of monomer) of stannous 2-ethylhexanoate (Sigma, Lot #1554). The reaction temperature was maintained between 170 and 190° C. under nitrogen for 4 hours. The reaction product melt was allowed to cool to 100° C., then diluted with a 200 ml addition of anhydrous toluene. The cooled reaction mixture was precipitated in a large excess of hexane (EM Sciences), collected on a coarse filter and dried to constant weight under vacuum at 40° C.

Characterization

Yield: 92.1 g dry weight

Trimethylene Carbonate D.P. 4.16 (NMR: Varian: Gemini 300 MHz)

Viscosity (10% w/w in deionized water) 15.79 Centipoise: (Brookfield Viscometer Model 201)

Example 9
Synthesis of PEG-Caprolactone Conjugates.

This example illustrates the synthesis of PEG-caprolactone conjugates. 100 g of polyethylene glycol (MW 8000) were heated to 100° C. in a propylene glycol bath. The melted PEG was evacuated to remove moisture, and then blanketed with argon. The evacuation was repeated three times. Vacuum-distilled epsilon-caprolactone (e-CL), 14 mls, was added to the molten PEG. The temperature was increased to 180° C. Stannous ethylhexanoate at a 200:1 monomer: catalyst mole ratio ratio was constituted in 0.5 mL of anhydrous toluene and added to the reaction mixture. After 4 hours at 180° C., the solution was cooled and diluted with 200 mL anhydrous toluene, and then precipitated in a large excess of hexane. The precipitated polymer was dried in a vacuum oven. The dry weight was 96.6 g.

Example 10
Synthesis of PEG-Caprolactone-Acrylate.

This example illustrates the synthesis of PEG-caprolactone conjugates capped by acrylation. 90 g of the PEG-caprolactone synthesized in Example 9 were added to a 1000 ml three-neck flask. 900 mL of anhydrous toluene were added, and 150 ml of the toluene were distilled off at 110° C. to remove water.

The solution was cooled to 60° C. and 8.5 mls of triethylamine were added, followed by 4.8 ml of acryloyl chloride, dropwise from a pipet. After 15 minutes, the reaction mixture was precipitated in hexane. The hexane precipitate was recovered on a medium Buchner funnel and dissolved in THF (tetrahydrofuran) at 40° C. on a water bath. The THF solution was then passed through 90 gm of alumina, prewetted with THF, on a Buchner funnel. The collected filtrate was evaporated to dryness on a rotary evaporator and placed under vacuum overnight. Yield was about 65 gm.

Example 11
Synthesis of Polyethylene Glycol-Glycolate Conjugates.

This example illustrates the synthesis of polyethylene glycol-glycolate conjugates. Commercial polyethylene glycol monomethoxy ether with number average molecular weight 5000 g/mole (PEG 5K) is thoroughly dried at 100° C. under a pressure of 10 mm Hg for 16 hr. A 100 ml round bottom flask and a magnetic stir bar are thoroughly flame dried and cooled under argon. 10 grams of dry PEG 5K monomethoxy ether, 1.16 gram of glycolide and 10 mg of stannous octanoate are charged under a nitrogen atmosphere into the flask. The reaction mixture is heated in an oil bath at 170° C. for 16 hr under an argon atmosphere. The product is dissolved in 20 ml methylene chloride and precipitated in 500 ml dry hexane. The copolymer is dried in a vacuum oven at 60° C. for 16 hr.

Example 12
Synthesis of Polyethylene Glycol-Glycolate (Trifunctional) Conjugates.

This example illustrates the synthesis of polyethylene glycol-glycolate (trifunctional) conjugates. The synthesis is conducted as described above in Example 11, but with 10 gram of ethoxylated trimethylolpropane triol (trifunctional polyethylene glycol with average molecular weight 1000 g/mole) and 17.4 grams of glycolide.

Example 13
Synthesis of PEG-(Glycolate)$_1$ (Caprolactate)$_4$ Acrylate.

This example illustrates the synthesis of PEG-(Glycolate)$_1$(Caprolactate)$_4$ acrylate. 100 g of polyethylene glycol, molecular weight 8000 g/mole, were dried by azeotroping off the moisture by distilling off toluene at 110° C. under argon atmosphere. The reaction mixture was dried further in vacuum at 120° C. for 1 hour to facilitate all removal of toluene. At the end of this drying period, the reaction mixture was brought up to 180° C.

Glycolide (Boehringer Ingelheim) was weighed out (2.339 g) in a dry box under nitrogen to prevent moisture from being present in the sample in trace amounts. Caprolactone (10.167 ml) was charged to the reactor vessel under nitrogen. Stannous octanoate, used as the catalyst in the ratio (1:100), was made up as a stock solution in anhydrous toluene, and added in a 100 ml quantity. The temperature of the reaction mixture was maintained between 180–190° C., under nitrogen, throughout the reaction time of 4 hours. At the end of 4 hours, the reaction mixture was cooled to 80–100° C., and 50 ml of anhydrous toluene (Aldrich) were added, with stirring. The toluene solution was poured into a large excess of hexane with vigorous vortexing. The precipitated powder was collected by filtration, and dried under vacuum at 40° C.

The PEG-(Gly)$_1$(Cap)$_4$—OH obtained from the step above was redissolved in 1000 ml of anhydrous toluene and 100 ml was distilled to azeotropically removed water. The reaction mixture was cooled to 65° C. under nitrogen. Triethylamine (2 molar excess) was added dropwise to the vigorously swirling reaction mixture. Previously distilled acryloyl chloride was added to 2 molar excess under nitrogen flush. Reaction time was 15 min. The hot reaction mixture was filtered through a medium porosity Buchner funnel, and precipitated in a large excess of hexane. The crude product was collected by filtration, redissolved in peroxide-free THF (tested for peroxides) and filtered hot through a medium mesh filter. The clear filtrate was filtered through an alumina bed (1:1) and precipitated in a large excess of hexane. The product was collected by filtration and dried in vacuum. Yield: 82 g.

Example 14
Topical Application of PEG-Polylactate Conjugates.

PEG-polylactate, a copolymer of the invention, was made essentially as in Example 1. Volunteers, who were familiar with exfoliants, tested the copolymer on their skin as follows: The skin of the fingers, or of the forehead, was dampened. Dry copolymer powder was applied to the fingers (and thereby dampened by the applied water) to determine the "feel" of the composition. The composition felt very "silky", and dried to invisibility without becoming tacky. Powder was then applied to the dampened forehead and allowed to dry.

Persistence was assessed by taste. Periodically, a clean, water-dampened finger was applied to the forehead and then to the tip of the tongue, to determine acidity by taste. Initially, there was no acidic taste, but within one hour of application an acidic taste was detected. Acid taste by this method persisted for at least six to eight hours. A comparison test with a commercial product containing monomeric hydroxy acids ("Alpha Hydrox" gel) gave an acid taste only for the first two to four hours. In addition, the application of the copolymer did not produce any persistent skin reddening or irritation. The skin was slightly pink for a few minutes just after application, similar to that obtained by the use of water on the face.

Example 15

Retinoic Acid Conjugates.

Retinoic acid was conjugated to PEG lactate diol via a hydrolysable ester bond. PEG lactate diol synthesized as in Example 1 (8.1 g) was azeotropically dried under reduced pressure (3×) using benzene. The dried PEG lactate diol, retinoic acid (0.90 g) and dimethylaminopyridine (catalytic) were dissolved in 50 mL dichloromethane. The reaction mixture was cooled to 0° C. with an ice bath. Dicylohexylcarbodiimide (0.62 g) in 2 mL of dichloromethane was slowly added. The reaction mixture was stirred for 24 hours (under foil cover), allowing the water bath to warm up to room temperature. The entire contents of the pot was dripped into swirling hexane (200 mL) to recover the yellow colored product. The crude product was rinsed twice with 100 mL of diethyl ether. The air dried crude product was redissolved in tetrahydrofuran (40 mL) and filtered to remove contaminating dicyclohexylurea. The filtrate was dripped into swirling hexane (200 mL). The purified product was recovered in a filter funnel and vacuum dried to yield a yellow solid (5.8 g).

An alternative approach would be to convert the retinoic acid to retinoyl chloride. The retinoyl chloride can then be used without isolation to react with the PEG lactate diol.

Coupling of other materials to the conjugates can readily be achieved by application of the procedures described above. For example, attachment of Eosin Y dye to polyethylene glycol-glycolate conjugates could be achieved as follows. 4.306 gram of polyethylene glycol-glycolate conjugate synthesized in Example 11 are dissolved in 100 ml dry acetone:benzene (1:1) mixture under an argon atmosphere. 0.081 gram of carbonyl diimidazole is added to the mixture and the reaction is continued at room temperature for 4 hours under argon. 1 gram Eosin Y, dissolved in 10 ml of acetone:benzene (1:1) mixture, is slowly added into the reaction mixture. The reaction is continued for 12 hours at room temperature under argon. The product is separated by repeated precipitation from methylene chloride into hexane.

Similarly, the attachment of peptides to polyethylene glycol-glycolide conjugates would be straightforward. 4.306 gram of polyethylene glycol-glycolide conjugate synthesized in Example 11 are dissolved in 100 ml dry DMF. 0.081 gram of carbonyl. diimidazole is added to the mixture and the activation reaction is continued at room temperature for 4 hours under argon atmosphere. 0.301 gram of RGD tripeptide (arginine-glycine-aspartic acid, a biologically active peptide known as a ligand for certain cell receptors) is slowly introduced into the reaction mixture. The reaction is continued for 6 hours and the product is separated by precipitating in a large excess of hexane.

Those skilled in the art will be able to ascertain, using no more than routine experimentation, many equivalents of the specific embodiments of the invention described herein. These and all other equivalents are intended to be encompassed by the following claims.

We claim:

1. A method for treatment of the skin, comprising topically applying an effective amount of a liquid or semi-solid formulation comprising one or more hydroxy acid copolymers in combination with a suitable carrier for topical application to skin in need of treatment, wherein the hydroxy acid copolymer comprises polymerized hydroxy acids covalently joined to at least one polymer block, and wherein the hydroxy acid copolymer has the formula $P_a H_b$, wherein P is a hydrophilic polymer block consisting predominantly of non-hydroxy acid subunits, H is a polymer block consisting predominantly of hydroxy acid subunits, a is the number of P blocks, b is the number of H blocks, a and b are integers of at least one, and the copolymer is either a linear, brush, star or branched copolymer, and wherein the copolymer further comprises groups capable of being polymerized to crosslink the block copolymers, and wherein the formulation is in a form selected from the group consisting of powders, gels, creams, ointments, emulsions, foams, aerosols, sprays, and lotions.

2. The method of claim 1 wherein the groups capable of being polymerized are ethylenically unsaturated.

3. The method of claim 2 wherein the groups are selected from the group consisting of unsaturated monocarboxylic groups, unsaturated dicarboxylic acids, unsaturated tricarboxylic acids, allyl groups, vinyl groups, and esters, ethers, and amides containing 12 or fewer carbons.

4. A method for making a liquid or semi-solid cosmetic formulation, comprising mixing one or more hydroxy acid copolymers in combination with a suitable carrier for topical application to skin in need of treatment, wherein the hydroxy acid copolymer comprises polymerized hydroxy acids covalently joined to at least one polymer block, and wherein the hydroxy acid copolymer has the formula $P_a H_b$, wherein P is a hydrophilic polymer block consisting predominantly of non-hydroxy acid subunits, H is a polymer block consisting predominantly of hydroxy acid subunits, a is the number of P blocks, b is the number of H blocks, a and b are integers of at least one, and the copolymer is either a linear, brush, star or branched copolymer and wherein the copolymer further comprises groups capable of being polymerized to crosslink the block copolymers, and wherein the formulation is in a form selected from the group consisting of powders, gels, creams, ointments, emulsions, foams, aerosols, sprays, and lotions.

5. The method of claim 1, wherein the polymerizable hydroxy acid copolymers are polymerized on the skin to form a gel coating.

6. The method of claim 4 wherein the polymerizable groups are ethylenically unsaturated.

7. The method of claim 6 wherein the groups are selected from the group consisting of unsaturated monocarboxylic groups, unsaturated dicarboxylic acids, unsaturated tricarboxylic acids, allyl groups, vinyl groups, and esters, ethers, and amides containing 12 or fewer carbons.

8. The method of claim 4, wherein the polymerizable hydroxy acid copolymers are polymerized on the skin to form a gel coating.

9. The method of claim 1 further comprising adding to the formulation materials selected from the group consisting of antibiotics, antifungals, pediculicides, antiperspirants, antipuritics, analgesics, anesthetics, blister treatments, canker sore treatments, insect bite treatments, diaper rash treatments, insect repellents, and sunscreens.

10. The method of claim 4 further comprising adding to the formulation materials selected from the group consisting of antibiotics, antifungals, pediculicides, antiperspirants, antipuritics, analgesics, anesthetics, blister treatments, canker sore treatments, insect bite treatments, diaper rash treatments, insect repellents, and sunscreens.

* * * * *